United States Patent [19]

Williams et al.

[11] Patent Number: 5,391,172
[45] Date of Patent: Feb. 21, 1995

[54] STENT DELIVERY SYSTEM WITH COAXIAL CATHETER HANDLE

[75] Inventors: Michael S. Williams, Chapel Hill, N.C.; Farhad Khosravi, Belmont; August Yambao, Fremont, both of Calif.

[73] Assignee: Advanced Cardiovascular Systems, Inc., Santa Clara, Calif.

[21] Appl. No.: 67,514

[22] Filed: May 24, 1993

[51] Int. Cl.⁶ .............................................. A61B 17/00
[52] U.S. Cl. ................................ 606/108; 606/198; 601/280
[58] Field of Search ..................... 606/1, 190–195, 606/198, 108; 604/96, 104, 107, 171, 264, 280, 158–164; 623/1, 12

[56] References Cited

U.S. PATENT DOCUMENTS

| | | | |
|---|---|---|---|
| 4,665,918 | 5/1987 | Garza et al. | 606/108 |
| 4,699,611 | 10/1987 | Bowden . | |
| 4,732,152 | 3/1988 | Wallsten et al. . | |
| 4,768,507 | 9/1988 | Fischell et al. | 606/108 |
| 4,892,539 | 1/1990 | Koch . | |
| 4,893,623 | 1/1990 | Rosenbluth . | |
| 4,990,151 | 2/1991 | Wallsten . | |
| 5,002,560 | 3/1991 | Machold et al. . | |
| 5,026,377 | 6/1991 | Burton et al. | 606/108 |
| 5,034,001 | 7/1991 | Garrison et al. . | |
| 5,089,005 | 2/1992 | Harada . | |
| 5,100,429 | 3/1992 | Sinofsky et al. . | |
| 5,108,416 | 4/1992 | Ryan et al. | 606/194 |
| 5,125,899 | 6/1992 | Frignoli | 604/187 |
| 5,156,620 | 10/1992 | Pigott . | |
| 5,163,952 | 11/1992 | Froix . | |
| 5,176,650 | 1/1993 | Haining | 604/164 |
| 5,190,058 | 3/1993 | Jones et al. . | |
| 5,192,297 | 3/1993 | Hull . | |
| 5,201,757 | 4/1993 | Heyn et al. | 623/1 |
| 5,290,295 | 3/1994 | Querals et al. | 623/1 |
| 5,290,310 | 3/1994 | Makower et al. | 606/108 |

Primary Examiner—Glenn Dawson
Attorney, Agent, or Firm—Fulwider, Patton, Lee & Utecht

[57] ABSTRACT

A stent delivery catheter handle for providing relative motion between the outer sheath of a stent delivery catheter and an underlying catheter, via a thumbswitch, to enable the outer sheath to withdraw from over the underlying catheter and expose a vascular prosthesis. The handle allows the annulus between the outer sheath and the underlying catheter to be filled with a purging fluid, to prevent blood from a patient's vascular system from entering the annulus and coagulating. A flush port forms a dynamic seal in the catheter handle.

19 Claims, 2 Drawing Sheets

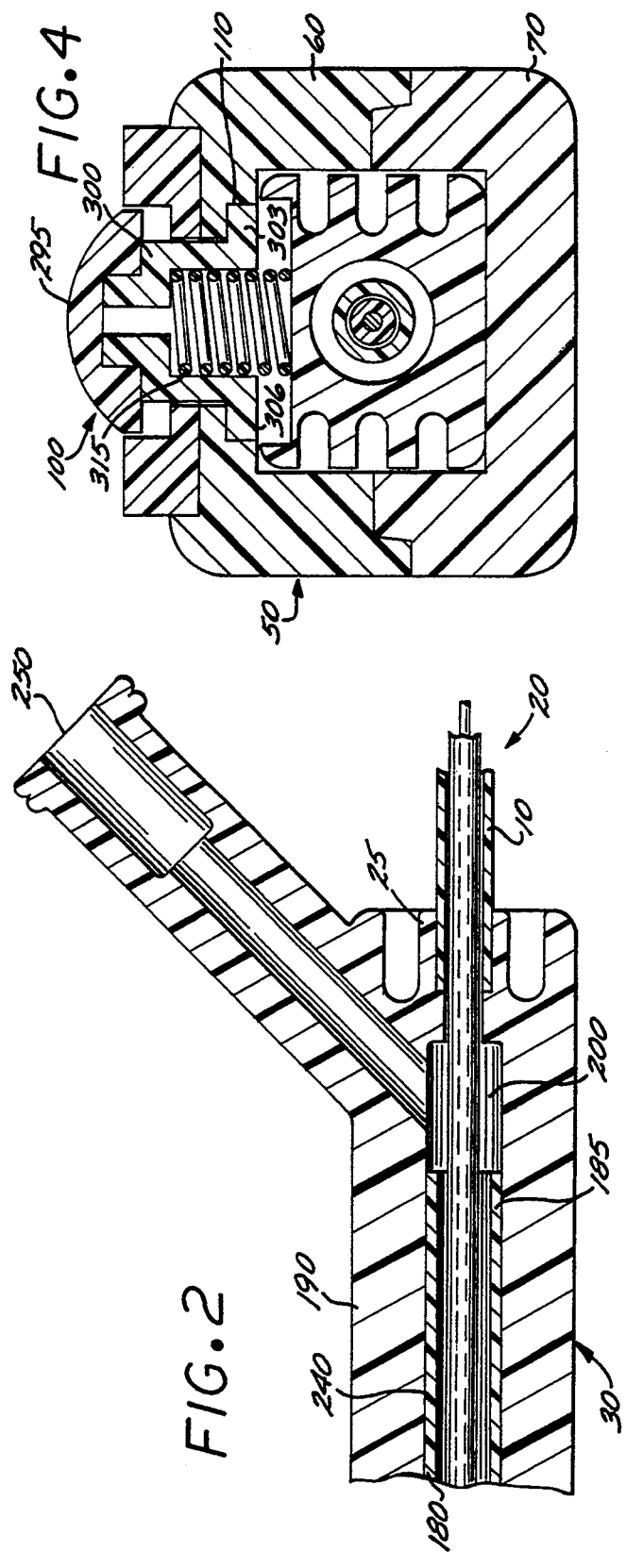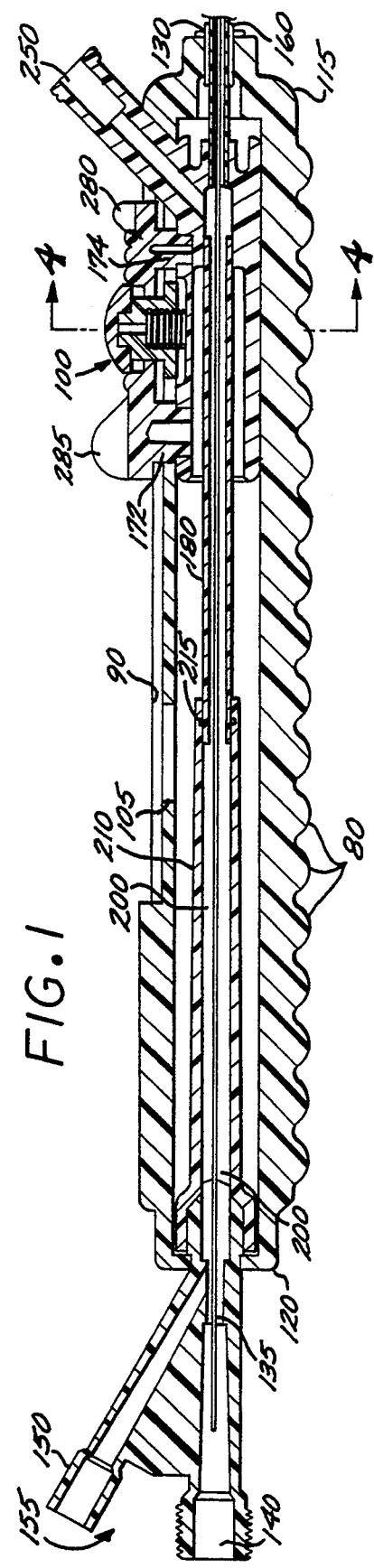

STENT DELIVERY SYSTEM WITH COAXIAL CATHETER HANDLE

BACKGROUND OF THE INVENTION

FIELD OF THE INVENTION

The invention relates to a retractable handle for use on a catheter.

In typical PTCA procedures, a guiding catheter is percutaneously introduced into the cardiovascular system of a patient through the brachial or femoral arteries and advanced through the artery until the distal end is in the ostium of the desired coronary artery. A guidewire and a dilatation catheter having a balloon on the distal end are introduced through the guiding catheter with the guidewire sliding within the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with radiopaque liquid at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery.

In angioplasty procedures of the kind referenced above, there may be restenosis of the artery, which may require another angioplasty procedure, a surgical bypass operation, or some method of repairing or strengthening the area. To help prevent restenosis and strengthen the dilated lesion area, a physician can implant an intravascular prosthesis, called a stent, for maintaining vascular patency inside the artery at the lesion. The stent is expanded to a larger diameter by the balloon portion of the catheter.

SUMMARY OF THE INVENTION

Expandable stents are often delivered by specialized catheters, such as the stent delivery catheter system found in commonly assigned, co-pending U.S. patent application Ser. No. 07/647,464 abandoned, filed Jan. 28, 1991 and incorporated herein in its entirety. This stent delivery catheter requires a manipulator to cause relative motion between a protective sheath that overlies the stent and the dilatation catheter underlying the sheath that is used to transport and expand the stent. The present invention is directed to providing one such manipulator.

More generally, the present invention is directed to providing a manipulator that will create relative motion in the cramped confines of a catheter or catheter-like mechanism. The present invention is not directed solely to balloon catheters. For example, the present invention may provide axial relative motion between concentric lumens in a stent delivery catheter of the kind that delivers a self expansive, wound up stent covered by an overlying sheath, with the sheath being withdrawn when the stent is to be expanded.

The present invention is further directed to preventing the possible accumulation of blood between the retractable sheath of a stent delivery catheter and the base catheter, which is undesirable as stagnated blood has the tendency to coagulate and cause thrombosis. To this end, the annulus between the outermost sheath and the underlying stent and catheter is filled with a fluid by a pressurized fluid source that introduces fluid though a port in the stent delivery catheter handle of the present invention.

Other uses for the present invention can be appreciated by those skilled in the art. These and other advantages of the invention will become more apparent from the following detailed description when taken in conjunction with the accompanying drawings.

BRIEF DESCRIPTION OF THE DRAWINGS

FIG. 1 is an axial cross-section depicting the manipulator of the present invention.

FIG. 2 is an enlarged view of a portion of the distal end of the manipulator of FIG. 1.

FIG. 4 is a cross-sectional view taken along line 4—4 of FIG. 1.

DETAILED DESCRIPTION OF THE PREFERRED EMBODIMENTS

Figure 3:
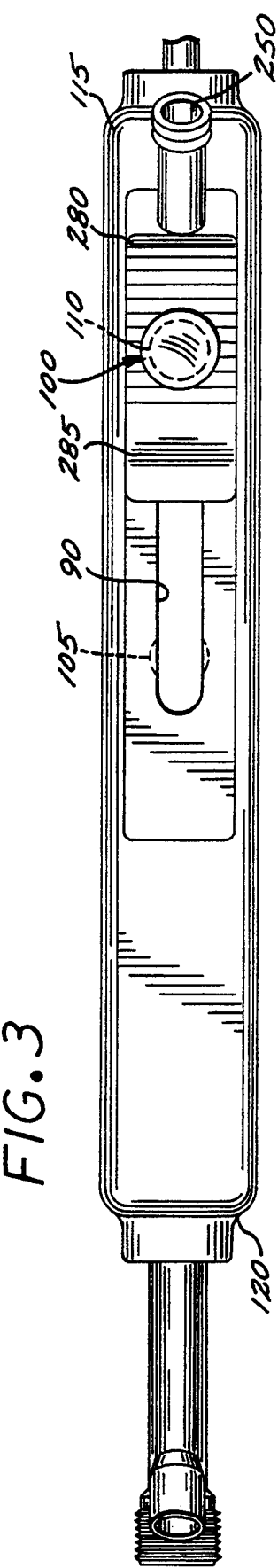
FIG. 3 is a top view of FIG. 1.
Figure 5:
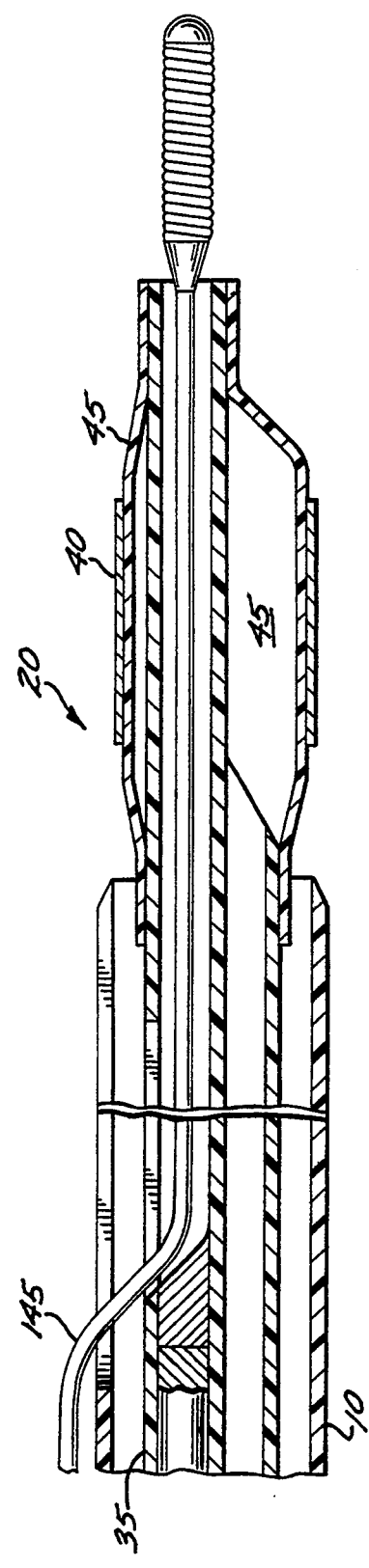
FIG. 5 depicts details of the sleeve retraction mechanism found on the distal portion of the stent delivery catheter of the preferred embodiment.

Referring to FIGS. 1-5, there is shown a preferred embodiment of the retractable sleeve stent delivery handle of the present invention. A retractable sheath 10 of a stent delivery catheter 20 is received by the distal nosepiece 25 of a slidable flush port and plunger assembly 30. The flush port and plunger assembly, as well as the entire handle, are generally coaxially disposed about the underlying catheter that they surround. As can be seen in FIG. 5, taken from FIG. 1 of the aforementioned co-pending application Ser. No. 07/647,464, abandoned retractable sheath 10 overlies the outer lumen 35 of the catheter, which is a rapid-exchange catheter. The retractable sheath 10 serves to protect an intravascular prosthesis or stent 40 that is disposed between the retractable sheath 10 and the outer lumen 35, on balloon portion 45. The retractable sheath 10 covers the stent during transport of the stent through the vasculature by the catheter. The sheath 10 is withdrawn from over the stent, to expose the stent, by the stent delivery handle of the present invention. Thereinafter the stent is expanded to engage the vasculature and the catheter is withdrawn.

As can be seen from FIGS. 1-5, the stent delivery handle has a housing body 50 made of a top half 60 and a bottom half 70, with each half made to fit into the other half. Bottom half 70 is provided with a finger grip 80, while top half 60 is provided with a thumb switch track that is formed by slot 90 along which a thumbswitch 100 reciprocates. The underside of slot 90 includes a pair of semicircular recesses 105, 110, situated towards the distal end 115 and proximal end 120 of the catheter handle tool, respectively, with the recesses engaged by laterally projecting semicircular locking arms 303, 306 on the thumbswitch 100. The locking arms serve to retain the thumbswitch along the slot at the recesses.

As can be seen from the figures, at the distal and proximal ends 115, 120 of the catheter handle tool there is provided a distal aperture 130 and a proximal aperture 135. At the proximal aperture is a Luer lock 155, as is known per se in the art. Though in the preferred embodiment of the present invention the catheter is shown as an rapid-exchange balloon catheter adapted to deliver a stent, in general any type of catheter may be employed, including a fixed wire catheter or any other device that requires a relative motion between a radially outermost and radially innermost sleeve.

The distal aperture 130 has a radius of about 5/64 inch sized to allow a typical catheter to slip through. At the distal aperture is a nosepiece 160.

Regarding the plunger and flush port assembly, there is shown a reciprocating plunger 180 having a distal end 185 that is attached to a sliding flush port assembly 190. Plunger 180 is hollow and coaxially disposed about the catheter assembly, as can be seen from the figures.

The flush port assembly 190 is attached to the outermost retractable sheath 10. The sheath 10 is moved relative to the underlying stent delivery catheter 20, in order to expose the underlying stent at the distal end of the catheter. The flush port assembly 190 is attached to the thumbswitch 100, via posts 172, 174. Reciprocating the thumbswitch along the track formed by slot 90 will also reciprocate the sliding flush port assembly along the slot, and therefore create relative motion between the retractable sheath 10 and the underlying stent delivery catheter 20 to retract sheath 10 from catheter 20. In order to prevent purging fluid or blood from exiting the catheter handle, the annulus 200, formed between the hollow interior of the plunger 180 and the underlying guidewire 145, is sealed from the outside. One area where purging fluid could escape is the interface between the plunger and the plunger chamber 210. To prevent fluid from escaping here, a dynamic packing or seal is formed by O-ring 215, which is received in a seal groove in the plunger to act as a dynamic seal between the plunger and plunger chamber. O-ring 215 thus seals fluid in annulus 200 from the atmosphere. Blood will never reach the handle because of the presence of the purging fluid column.

Turning again to FIGS. 1 and 4, it can be seen that the flush port and plunger assembly 30 comprises a plunger 180, which slides inside the plunger chamber 210. The plunger is reciprocated by the thumbswitch 100, attached to the plunger through two vertical posts 172, 174. The vertical posts 172, 174 slide within thumbswitch slot 90. As the plunger is withdrawn distally towards the Luer fitting 155 of the handle by the thumbswitch, retractable sleeve 10 is withdrawn axially from the distal to the proximal end of the stent, to expose the stent.

Turning attention again to FIGS. 1 and 2, further details of the flush port feature of the present invention will now be described. Disposed between plunger 180 and the outer retractable sleeve 10 is flush port assembly 190. The outer retractable sleeve 10 is connected to the flush port assembly at the distal end nosepiece 25 of the flush port assembly, while the plunger 180 is connected to the flush port assembly at portion 240 of the flush port assembly. The retractable sleeve 10 may be attached to nosepiece 25 by any suitable means, such as gluing.

Note that annulus 200 is exposed to the blood pressure in a patient's cardiovascular system. As a consequence, in the absence of any counter pressure in this annulus, it is possible for blood to flow inside this annulus and towards the proximal end of the catheter, where it may coagulate and cause thrombosis. To rectify this problem, the present invention allows for a flushing or purging fluid, under pressure, to be introduced into the annulus 200 via a flush port 250 that is part of flush port assembly 190. The flush port is an orifice extending radially from the outside into annulus 200. The flush port may be used for distal site specific drug delivery, and may be used to introduce radiopaque fluid into the vasculature for distal angiographic injections. The flush port thus allows fluid communication between the annulus 200 and the outside, to allow purging or flushing fluid under pressure to be introduced into the annulus. The flush port slides along the same longitudinally extending slot 90 formed for thumbswitch 100. The flush port may be capped by a suitable valve, that can be opened to introduce purging fluid into annulus 200. The purging fluid is introduced under slight pressure, prior to entry into the vasculature, and prevents any blood from stagnating in annulus 200. In addition, the purging fluid may serve as a lubricant or to introduce radiopaque marker fluid into a vasculature.

Referring to FIGS. 1 and 4, there are shown a cross-sectional view of the thumbswitch 100 and thumbswitch pushbutton locking mechanism. The thumbswitch has a knurled surface 80 for better gripping. Thumbswitch 100 has a distal thumb grip portion 280, a proximal thumb grip portion 285, and vertical posts 172, 174, that connect the thumb grip portion with the flush port and plunger assembly 30.

The thumbswitch includes a pushbutton locking mechanism having a pushbutton 295 connected to a cap shaped member 300. The sleeve retraction thumbswitch is locked into place on the catheter handle by having cap shaped member 300 engage spaced semicircular recesses 105, 110, via laterally projecting semicircular arms 303, 306. The spaced recesses are located on the underside of the housing top half 60, along the underside of slot 90, and are locations where the thumbswitch may be locked to fix the retraction of sleeve 10. The recesses may be spaced at a plurality of locations, to give a plurality of stops. The cap shaped locking member 300 and pushbutton 295 are spring biased upwards with respect to the plunger and flush port assembly 190 by a spring 315, that continuously forces the cap shaped locking member against the underside of slot 90 in the upper portion 60 of housing 50.

While in the preferred embodiment a spring biased pushbutton locking device is shown to lock the thumbswitch in a fixed position along said thumbswitch slot, it is envisioned that any other equivalent means can be used to lock the thumbswitch, including dispensing with the pushbutton assembly shown and providing tabs along the slot to frictionally engage posts 172, 174. The specific embodiment of the present invention has been described above in connection with a specialized catheter designed to deliver stents, however, it is within the scope of the present invention that the present invention may be used with any type of catheter or any other medical instrument.

While specific embodiments of the invention have been described in detail, it will be appreciated by those skilled in the art that various modifications to the structure and use of the disclosed invention may be made in light of the overall teachings of the disclosure, without departing from the scope of the invention as defined by the appended claims.

We claim:

1. A stent delivery system comprising:
   a stent delivery catheter assembly having a delivery catheter, a handle housing coaxially positioned on a proximal end of said delivery catheter, a balloon portion on a distal end of said delivery catheter, a stent mounted on said balloon portion, and a sheath overlying said delivery catheter and adapted for relative axial movement with respect to said delivery catheter; and a plunger assembly enclosed by said handle housing, said plunger assembly connected to said sheath, whereby movement of said plunger assembly proximally provides relative motion between said sheath and said delivery catheter, to retract said sheath proximally from overlying said stent on said balloon portion.

2. The stent delivery system of claim 1, wherein said handle housing has a plunger chamber, and said plunger assembly is received by said plunger chamber.

3. The stent delivery system of claim 2, further comprising:
a thumbswitch operatively connected to said sheath, wherein retracting said thumbswitch retracts said sheath from said stent.

4. The stent delivery system of claim 3, wherein said handle housing has a slot therein, and said thumbswitch slides within said slot.

5. The stent delivery system of claim 4, wherein:
an annulus is formed between said sheath and said delivery catheter, and further comprising a port in fluid communication with said annulus and radially extending from said annulus to outside atmosphere, wherein fluid may be introduced into said annulus.

6. The stent delivery system of claim 5, wherein said port comprises a port assembly operatively connected to said plunger assembly, said port assembly connected to said thumbswitch, and said port sliding within said slot.

7. The stent delivery system of claim 6 further comprising a pushbutton on said thumbswitch, said pushbutton operatively connected to a locking device, said handle housing having an upper and a lower portion, said upper portion containing said slot, an underside of said upper portion having a plurality of recesses, said locking device being spring biased upwards to engage one of said recesses, to lock said thumbswitch in a fixed position on said slot.

8. The stent delivery system handle of claim 7, wherein said lower portion contains a plurality of finger wells forming a handgrip.

9. The stent delivery system of claim 1, wherein said plunger assembly is hollow and coaxially disposed about said delivery catheter.

10. The stent delivery system of claim 9, wherein said plunger assembly comprises a plunger and a plunger chamber, said plunger being received by said plunger chamber providing a dynamic seal therebetween.

11. The stent delivery system of claim 10, wherein said dynamic seal is formed by an O-ring.

12. A stent delivery system comprising:
a stent delivery catheter assembly having a handle housing coaxially positioned on a proximal end of a delivery catheter, said delivery catheter having a balloon portion on a distal end, a stent mounted on said balloon portion, and a sheath overlying said delivery catheter and adapted for relative axial movement with respect to said delivery catheter; and a thumbswitch operably connected to said sheath and slidably retained in said handle housing, whereby retracting said thumbswitch proximally retracts said sheath proximally relative to said delivery catheter.

13. The stent delivery system according to claim 12, wherein said handle housing has a slot to allow said thumbswitch to reciprocate along said slot.

14. The stent delivery system according to claim 13, wherein said thumbswitch includes means for locking said thumbswitch in a fixed position on said slot.

15. The stent delivery system according to claim 14, wherein said means for locking comprises a pushbutton on said thumbswitch, said pushbutton operatively connected to a locking device, said handle housing having an upper portion that contains said slot and an underside of said upper portion having a plurality of recesses, said locking device being spring biased upwards to engage one of said recesses, to lock said thumbswitch in a fixed position on said slot.

16. The stent delivery system according to claim 12, wherein
an annulus is formed between said sheath and said delivery catheter, and further comprising a port in fluid communication with said annulus, wherein fluid may be introduced into said annulus via said port.

17. The stent delivery system according to claim 16, wherein said handle housing has a slot therein, and said port reciprocates along said slot.

18. The stent delivery system according to claim 17, further comprising a plunger connected to said thumbswitch, and a plunger chamber connected to said handle housing, said plunger being hollow and receiving said delivery catheter therein, said plunger received by said plunger chamber and providing a dynamic seal to prevent fluid communication between said annulus and atmosphere.

19. The stent delivery system according to claim 18, wherein said dynamic seal is provided by an O-ring surrounding said plunger and providing a seal between said plunger and said plunger chamber.

* * * * *